(12) United States Patent
Amaral et al.

(10) Patent No.: US 7,452,681 B2
(45) Date of Patent: Nov. 18, 2008

(54) DIAGNOSTIC METHODS FOR THE DETECTION OF AUTISM SPECTRUM DISORDER

(75) Inventors: David G Amaral, Davis, CA (US); Judy Van de Water, Capay, CA (US)

(73) Assignee: The Regents of the University of California, Okaland, CA (US)

( * ) Notice: Subject to any disclaimer, the term of this patent is extended or adjusted under 35 U.S.C. 154(b) by 0 days.

(21) Appl. No.: 11/381,943

(22) Filed: May 5, 2006

(65) Prior Publication Data
US 2006/0292640 A1    Dec. 28, 2006

Related U.S. Application Data

(60) Provisional application No. 60/678,670, filed on May 5, 2005.

(51) Int. Cl.
G01N 33/53      (2006.01)
G01N 33/567     (2006.01)
G01N 33/566     (2006.01)
C07K 16/00      (2006.01)
C07K 17/00      (2006.01)

(52) U.S. Cl. .................. 435/7.1; 435/7.21; 435/7.9; 436/501; 436/503; 530/387.1; 530/391.3

(58) Field of Classification Search .................. None
See application file for complete search history.

(56) References Cited

OTHER PUBLICATIONS

Ashwood, P., et al., "A review of autism and the immune response," *Clinical and Developmental Immunology*, vol. 11(2), pp. 165-174 (Jun. 2004).
Ashwood, P., et al., "Is autism an autoimmune disease?" *Autoimmune Rev.*, vol. 3(7-8), 13 pgs. (Nov. 2004).
Bauman, M., et al., "The development of mother-infant interactions after neonatal amygdale lesions in rhesus monkeys," *The Journal of Neuroscience*, vol. 24(3), pp. 711-721 (Jan. 21, 2004).
Bauman, M., et al., "The development of social behavior following neonatal amygdale lesions in rhesus monkeys," *Journal of Cognitive Neuroscience*, vol. 16(8), pp. 1388-1411 (2004).
Connolly, A., et al., "Serum autoantibodies to brain in Landau-Kleffner variant, autism, and other neurologic disorders," *The Journal of Pediatrics*, vol. 134(5), pp. 607-613 (May 1999).
Cook, E., et al., "Receptor inhibition by immunoglobulins: Specific inhibition by autistic children, their relatives, and control subjects," *Journal of Autism and Developmental Disorders*, vol. 23(1), pp. 67-78 (1993).
Croen, L., et al., "Maternal autoimmune diseases, asthma and allergies, and childhood autism spectrum disorders," *Arch. Pediatr. Adolesc. Med.*, vol. 159, pp. 151-157 (Feb. 2005).
Dalton, P., et al., "Maternal neuronal antibodies associated with autism and a language disorder," *Annals of Neurology*, vol. 53(4) pp. 533-537 (Apr. 2003).
Eigsti, I-M., et al., "A systems neuroscience approach to autism: Biological, cognitive and clinical perspectives," *Mental Retardation and Developmental Disabilities*, Research Reviews, vol. 9, pp. 206-216 (2003).
Emery, N., et al., "The effects of bilateral lesions of the amygdala on dyadic social interactions in rhesus monkeys (*Macaca mulatta*)," *Behavioral Neuroscience*, vol. 115(3), pp. 515-544 (2001).
Gothard, K., et al., "How do rhesus monkeys (*Macaca mulatta*) scan faces in a visual paired comparison task?" *Anim. Cogn.*, vol. 7, pp. 25-36 (2004).
Flannery, K., et al., "A test of the immunoreactive theory for the origin of neurodevelopmental disorders in the offspring of women with immune disorder," *Cortex*, vol. 30, pp. 635-646 (1994).
Kiessling, L., et al., "Antineuronal antibodies: Tics and obsessive-compulsive symptoms," *Developmental and Behavioral Pediatrics*, vol. 15(6), pp. 421-425 (Dec. 1994).
Plioplys, A., et al., "Anti-CNS antibodies in childhood neurologic diseases," *Neuropediatrics*, vol. 20, pp. 93-102 (1989).
Plioplys, A., et al., "Lymphocyte function in autism and rett syndrome," *Neuropsychobiology*, vol. 29, pp. 12-16 (1994).
Prather, M., et al., "Letter to Neuroscience: Increased social fear and decreased fear of objects in monkeys with neonatal amygdale lesions," *Neuroscience*, vol. 106(4), pp. 653-658 (2001).
Shamy, J., et al., Hippocampal volume is preserved and fails to predict recognition memory impairment in aged rhesus monkeys (*Macaca mulatto*), *Neurobiology of Aging*, 11 pgs. (2005).
Singh, V., et al., "Immunodiagnosis and immunotheraphy in autistic children," *Ann. NY Acad. Sci.*, vol. 540, pp. 602-604 (1994).
Singh, V., et al., "Antibodies to myelin basic protein in children with autistic behavior," *Brain, Behavior, and Immunity*, vol. 7, pp. 97-103 (1993).
Singh, V., et al., "Circulating autoantibodies to neuronal and glial filament proteins in autism," *Pediatric Neurology*, vol. 17(1), pp. 88-90 (1997).
Singh, et al., "Prevalence of serum antibodies to caudate nucleus in autistic children," *Neuroscience Letters*, vol. 355, pp. 53-56 (2004).
Silva, S., et al., "Autoantibody repertoires to brain tissue in autism nuclear families," *Journal of Neuroimmunology*, vol. 152, pp. 176-182 (2004).
Sparks, B., et al., "Brain structural abnormalities in young children with autism spectrum disorder," *Neurology*, vol. 59, pp. 184-192 (Jul. 2002).
Todd, R., et al., "Demonstration of inter- and intraspecies differences in serotonin binding sites by antibodies from an autistic child," *PNAS*, vol. 82, pp. 612-616 (Jan. 1985).
Vargas, D., et al., "Neuroglial activation and neuroinflammation in the brain of patients with autism," *Ann. Neurol.*, vol. 57, pp. 67-81 (2005).
Warren, R., et al., "Detection of maternal antibodies in infantile autism," *J. Am. Acad. Child Adolesc. Psychiatry*, vol. 29(6), pp. 873-877 (Nov. 1990).
Weizman, A., et al., "Abnormal immune response to brain tissue antigen in the syndrome of autism," *Am. J. Psychiatry*, vol. 139(11), pp. 1462-1465 (Nov. 1982).

*Primary Examiner*—Olga N Chernyshev
(74) *Attorney, Agent, or Firm*—Townsend and Townsend and Crew LLP

(57) ABSTRACT

The present invention provides methods of identifying markers indicative of the risk of developing a neurodevelopmental disorder caused in part by antibody- or autoantibody-mediated damage of neural tissue, including autism spectrum disorder (ASD). The invention further provides methods of diagnosing whether an individual has a neurodevelopmental disorder, including an ASD, and methods for determining the risk that a mother's future offspring will develop an a neurodevelopmental disorder, including an ASD.

18 Claims, 6 Drawing Sheets

Neural Tissue Western Blot- Adult brain fractions

Immunohistochemistry of non-human primate cerebellum

DIAGNOSTIC METHODS FOR THE DETECTION OF AUTISM SPECTRUM DISORDER

CROSS REFERENCE TO RELATED APPLICATIONS

This application claims the benefit of U.S. Provisional Patent Application No. 60/678,670, filed May 5, 2005, the entire disclosure of which is hereby incorporated herein by reference.

STATEMENT AS TO RIGHTS TO INVENTIONS MADE UNDER FEDERALLY SPONSORED RESEARCH AND DEVELOPMENT

This invention was made with Government support under Grant No. ES11269, awarded by the National Institutes of Health. The Government has certain rights in this invention.

FIELD OF THE INVENTION

The present invention relates to diagnostic methods for detecting the risk of an individual for developing a neurodevelopmental disorder, including an autism spectrum disorder, by determining the presence of antibodies against brain tissue and identifying the brain regions, cell types and proteins targeted by the antibodies.

BACKGROUND OF THE INVENTION

Autism spectrum disorders (ASD) are a neurodevelopmental disorders manifested by a spectrum of behavioral anomalies characterized by impaired social interaction and communication, often accompanied by repetitive and stereotyped behavior. The characteristic impairments may be accompanied by mental retardation and/or epilepsy. The condition becomes apparent within the first 3 years of life and persists into adulthood. In a majority of cases, there is no unequivocally normal period(s) in the child's development (classic autism). Usually, social development is markedly delayed and deviant, and language fails to appear or progress normally. In a smaller group of cases, parents report a period of normal development followed by regression, occasionally abrupt, in the child's language, sociability and play.

The current incidence of autism spectrum disorders is about 1:250 of the total population. The male to female ratio is about 4:1. There has been about a 5-fold increase in the last 10 years in new cases of ASD in the pediatric population of children aged 1.5-6 years. This does not reflect the major increase in newly diagnosed cases prior to 1994 when the diagnostic criteria changed.

There are numerous hypotheses regarding the etiology and pathology of ASD, including a suggested role for immune dysfunction. Autoantibodies against CNS proteins, including neuron-axon filament proteins (NAFP), cerebellar neurofilaments, myelin basic protein (MBP), brain endothelial cells, caudate nucleus, serotonin receptors have been reported in a subset of ASD patients (reviewed in Ashwood and Van de Water, *Autoimmun Rev* (2004) 3:557-62). There currently exists no genetic or biologic test for diagnosing autism spectrum disorders (ASD). Accordingly there remains a need for understanding the etiology of ASD and for diagnostic tests predictive of an individual's risk for developing the symptoms indicative of an ASD, allowing for early intervention in the treatment of this neurodevelopmental disorder. The present invention fulfills this and other needs.

BRIEF SUMMARY OF THE INVENTION

The present invention provides methods for identifying one or more markers indicative of a neurodevelopmental disorder, including an autism spectrum disorder (ASD), the methods comprising determining the presence or absence, or differential presence, of an autoantibody directed against a neural antigen in a sample from an individual having a neurodevelopmental disorder; and detecting a pattern of staining of brain regions and cell types bound by the autoantibody, wherein the marker indicative of a neurodevelopmental disorder is identified by the presence of the autoantibody in the sample and the pattern of staining in the brain that is indicative of a neurodevelopmental disorder.

The invention further provides for methods of diagnosing a neurodevelopmental disorder in an individual, the method comprising determining the presence or absence, or differential presence, of an autoantibody in a sample from the individual, wherein the autoantibody is directed against a neural antigen located in one or more regions of the brain selected from the group consisting of the cerebellum, the hypothalamus, the amygdala and the orbitofrontal cortex, wherein the presence of the autoantibody indicates that the individual has a neurodevelopmental disorder, and wherein the autoantibody was previously identified according the methods described herein.

The invention also provides methods for determining a risk of a neurodevelopmental disorder in a mother's future offspring, the method comprising determining the presence or absence, or differential presence, of an antibody directed against a neural antigen in a sample from the mother during a prenatal period; and detecting a pattern of staining of brain regions and cell types bound by the antibody, wherein the presence of the antibody in the sample and a pattern of staining in the brain that is indicative of a neurodevelopmental disorder indicates a risk of a neurodevelopmental disorder in the mother's future offspring.

In a related aspect, the invention provides methods for determining the pathological process of a neurodevelopmental disorder, comprising:

a) exposing a non-human primate fetus to a known causative factor of the neurodevelopmental disorder;

b) after birth and up until weaning, raising the infant subject primate with its mother and a primate social group comprising at least two other mother-infant primate pairs and at least one male primate;

c) following weaning, determining at least one developmental indicator selected from the group consisting of neurological status, social performance, emotional performance, behavioral performance and cognitive performance.

In a further aspect, the invention provides methods for determining the causative factor of a neurodevelopmental disorder, comprising:

a) exposing a non-human primate fetus to a putative or suspected causative factor of a neurodevelopmental disorder;

b) after birth and up until weaning, raising the infant subject primate with its mother and a primate social group comprising at least two other mother-infant primate pairs and at least one male primate;

c) following weaning, determining at least one developmental indicator selected from the group consisting of neurological status, social performance, emotional performance, behavioral performance and cognitive performance.

DEFINITIONS

The term "neurodevelopmental disorder" refers to any condition, disease, disorder characterized by abnormal neurodevelopment and/or basic biobehavioral processes, including attentional and perceptual processing, executive function, inhibitory control (e.g., sensory gating), social cognition, and communication and affiliative behaviors. Exemplified neurodevelopmental disorders include attention deficit hyperactivity disorder, schizophrenia, obsessive-compulsive disorder, mental retardation, and autistic spectrum disorders. Some neurodevelopmental disorders are at least in part caused by antibody-mediated or autoantibody-mediated damage to neural tissue, including for example, autistic spectrum disorders, opsoclonus-myoclonus syndrome (OMS) (Pranzatell, et al., *Pediatrics* (2005) 115:e115-9), obsessive-compulsive disorder (OCD) and tics (Kiessling, et al., *J Dev Behav Pediatr* (1994) 15:421-5), cerebral palsy, mental retardation, seizures, articulation disorder, learning disabilities (i.e., reading or arithmetic), verbal or performance aptitude deficits, and attention deficit disorder (Flannery, *Cortex* (1994) 30:635). See also, Johnson, *Bioessays* (2003) 25:464-77. Further information on neurodevelopmental disorders can be found, for example, through the Neurodevelopmental Disorders Branch of the National Insitute of Mental Health (worldwide website address at nihm.nih.gov/dptr/b2-nd-.cfm). Additional information on neurodevelopmental disorders can be found, for example, in *Developmental Disabilities in Infancy and Childhood: Neurodevelopmental Diagnosis and Treatment*, Capute and Accardo, eds. 1996, Paul H Brookes Pub Co.; Hagerman, *Neurodevelopmental Disorders: Diagnosis and Treatment*, 1999, Oxford Univ Press; *Handbook of Neurodevelopmental and Genetic Disorders in Children*, Goldstein and Reynolds, eds., 1999, Guilford Press; *Handbook of Neurodevelopmental and Genetic Disorders in Adults*, Reynolds and Goldstein, eds., 2005, Guilford Press; and *Neurodevelopmental Disorders*, Tager-Flusberg, ed., 1999, MIT Press.

The term "autism spectrum disorder" or "autistic spectrum disorder" interchangeably refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into "high functioning autism" or "low functioning autism," depending on the extent of social interaction and communication impairment. Individuals diagnosed with "high functioning autism" have minimal but identifiable social interaction and communication impairments (i.e., Asperger's syndrome). Additional information on autism spectrum disorders can be found in, for example, *Autism Spectrum Disorders: A Research Review for Practitioners*, Ozonoff, et al., eds., 2003, American Psychiatric Pub; Gupta, *Autistic Spectrum Disorders in Children*, 2004, Marcel Dekker Inc; Hollander, *Autism Spectrum Disorders*, 2003, Marcel Dekker Inc; and *Handbook of Autism and Developmental Disorders*, Volkmar, ed., 2005, John Wiley.

By "specifically binds" or "specific binding" is intended that an antibody preferentially binds to an antigen over other antigens.

DETAILED DESCRIPTION

General

Figure 1:
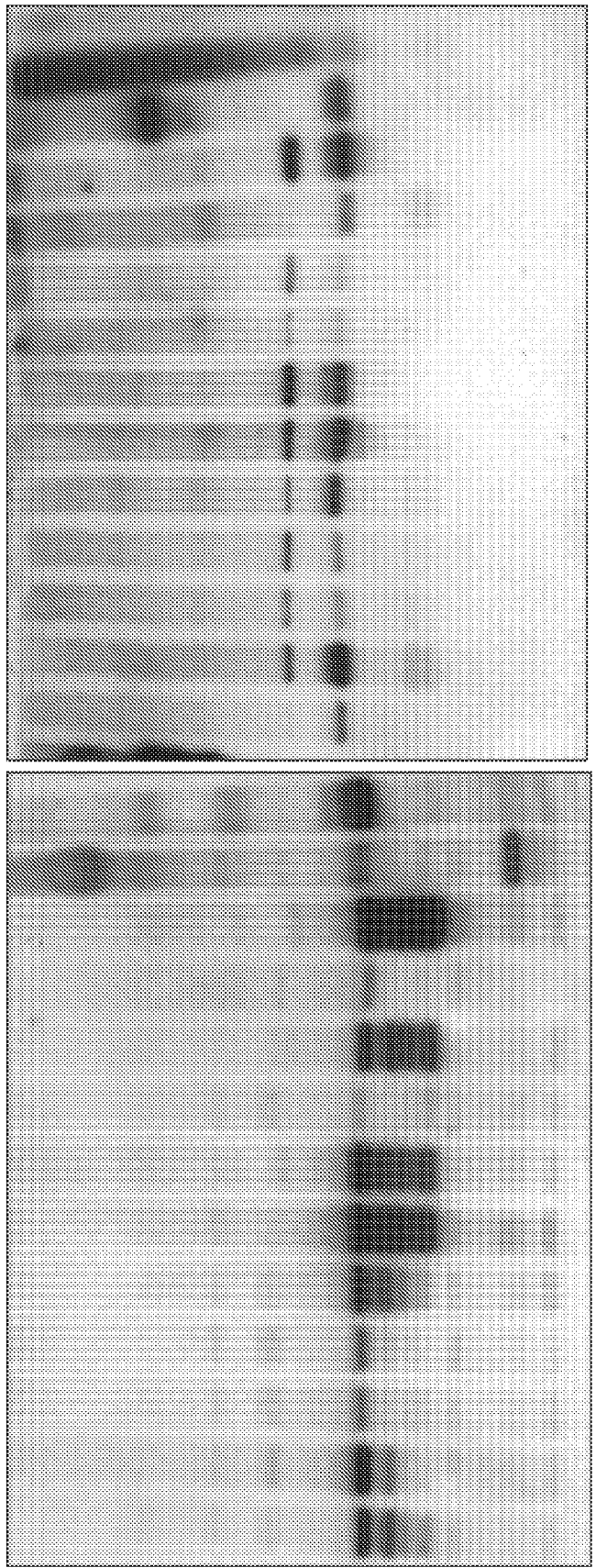
FIG. 1 illustrates exemplified Western immunoblots of adult brain extract (i.e., homogenized brain tissue) fractions from different brain regions exposed to the serum from an individual having an ASD and from an individual not having an ASD. Serum dilutions are 1:1000. Am=amygdala; Cr=cerebellum; CC=cerebral cortex; Fl=frontal lobe; Hp=hippocampus; Ht=hypothalamus; Bs=brainstem; Tl=temporal lobe; Th=thalamus; Fb=fetal brain; Sc=spinal cord; Sm=smooth muscle; and K=kidney.

The present invention evaluates the presence or absence, or differential presence, of antibodies or autoantibodies in an individual against one or more neural antigens in brain tissue. The presence of such antibodies or autoantibodies and the localized brain regions, cell types and/or polypeptides that they specifically bind are indicators of potential sources for brain damage and/or autoimmune markers. Identifying autoantibodies and the localized brain regions to which they bind in an individual provides a definitive assay for distinguishing neurodevelopmental disorders, including autism spectrum disorders. The methods of the present invention provide diagnostic tests for individuals suspected of having a neurodevelopmental disorder, particularly a neurodevelopmental disorder caused by (auto)antibody mediated damage to neural tissue, including an autism spectrum disorder, that allow for early intervention in their treatment. Identifying antibodies in a potential mother and the localized brain regions to which they bind provides indicators of potential sources for brain damage in a developing fetus that could lead to neurodevelopmental disorders, including an ASD. The methods of the present invention further provide diagnostic tests for potential mothers-to-be that allow for removal of harmful antibodies and prevention of brain damage that could lead to neurodevelopmental disorders, including an ASD.

The methods of the invention generally employ a two-prong approach, using the complementing techniques of identifying components of brain tissue extracts bound by (auto)antibodies and then identifying the in situ location of such components in brain tissue sections, for instance, using immunohistochemistry. In the first prong, components of brain tissue extracts are separated and contacted with a tissue sample from an individual to detect polypeptides specifically bound by antibodies or autoantibodies present in the tissue sample. In the second prong, brain sections, including from, for example, human cadavers, non-human primates, or fetal tissue are contacted with the tissue sample from the individual to identify the brain regions, cell types, and overall binding pattern of in situ brain tissue bound by the antibodies or autoantibodies. The order in which the immunoassay or the immunohistochemistry evaluations are carried out is not critical to the invention.

Detailed Embodiments

Methods of Identifying Markers

The present invention provides methods for identifying one or more markers indicative of a neurodevelopmental disorder, including an autism spectrum disorder (ASD), the methods comprising determining the presence or absence, or differential presence, of an autoantibody directed against a neural antigen in a sample from an individual having a neurodevelopmental disorder; and detecting a pattern of staining of brain regions and cell types bound by the autoantibody, wherein the marker indicative of a neurodevelopmental disorder is identified by the presence or absence, or differential presence, of the autoantibody in the sample and the pattern of staining in the brain that is indicative of a neurodevelopmental disorder.

The invention also provides methods for determining a risk of developing a neurodevelopmental disorder, including an autism spectrum disorder, in a mother's future offspring, the method comprising determining the presence or absence, or differential presence, of an antibody directed against a neural antigen in a sample from the mother during a prenatal period; and detecting a pattern of staining of brain regions and cell types bound by the antibody, wherein the presence of the antibody in the sample and a pattern of staining in the brain that is indicative of a neurodevelopmental disorder indicates a risk of a neurodevelopmental disorder in the mother's future offspring. Typically, the neural antigen is a fetal neural antigen.

Generally, the sample from the individual (e.g., a patient or a potential mother) being tested for identification or diagnosis is a fluid tissue sample, for example, blood, serum, plasma or cerebrospinal fluid.

In carrying out the step of determining the presence or absence, or differential presence, of an autoantibody or antibody against a neural antigen, the sample from the individual is contacted with the components of a brain extract. The brain extract is usually from a non-human primate, a human cadaver, a human fetus, or a non-human primate fetus. In certain instances, it is appropriate to use a brain extract from a mammal, for example, from a pig, dog, cat, rat, or mouse. The brain extract can be prepared from a whole brain, including portions of the spinal cord, or can be from specific brain regions or subregions. For example, a brain extract can be prepared from one or more brain regions including, for example, right or left cerebral hemispheres, frontal, parietal, temporal, or occipital lobes and brain stem. Brain extract can also be prepared from one or more specific subregions of the brain, including, for example, the cerebellum, hypothalamus, dorsal thalamus, hippocampus, amygdala, caudate nucleus, cerebral cortex, orbitofrontal cortex, neocortex, medulla, midbrain, pons, and spinal cord. Specific regions and subregions of the brain are well known in the art. Brain anatomy definitions can be found in, for example, Purves, et al., *Neuroscience*, McNamara and Williams, eds., 2001, Sinauer Associates, Inc.

The components of a brain extract are usually separated according to one or more properties so that they can be individually detected. For example, brain extract components (i.e., protein, carbohydrates, lipids and nucleic acids), can be separated according one or more parameters including, for example, size, charge, hydrophilicity or hydrophobicity. In one embodiment brain extracts are separated according to size, for example, using liquid chromatography or sodium dodecyl sulfate polyacrylamide gel electrophoresis (SDS-PAGE) techniques well known in the art. When separating brain extract components using SDS-PAGE, straight percentage (i.e., 8%, 10%, 12%, 15%) or gradient percentage (i.e., 4-20%) acrylamide gels can be used in the present methods. When separating brain extract components according to charge, well known techniques, including isoelectric focusing or mass spectrometry can be used. Well known liquid chromatography methods, including high performance liquid chromatography (HPLC) or fast performance liquid chromatography (FPLC) can be used to separate components according to size, charge, hydrophilicity or hydrophobicity. The particular method and parameter for separation of brain extract components is not critical, so long as a sufficient amount of the separated components is available for exposure to a sample from an individual. In one embodiment, brain extract components are first separated according to size and then separated according to charge, for instance, using 2-dimensional gel electrophoresis. In one embodiment, the brain extract components are separated according to size. General strategies for separating polypeptides in brain extract preparations can be found, for example, in Cutler, *Protein Purification Protocols*, $2^{nd}$ edition, 2004, Humana Press; and in Roe, *Protein Purification Applications: A Practical Approach*, $2^{nd}$ edition, 2001, Oxford University Press.

After separation into individually detectable components, the brain extract components are transferred to a substrate that sufficiently adheres the components, by covalent or non-covalent binding, such that the components can be directly contacted with a sample from an individual. For example, if separating the brain extract components using an acrylamide gel, it is convenient to transfer the separated components onto a membrane suitable for immunoblotting (i.e., nitrocellulose). If separating the brain extracts using liquid chromatography, it is convenient to collect the separated, eluted components in a multi-well plate, for example, a 96-well plate, a 192-well plate, a 384-well plate, or a 1536 well-plate (commercially available from Corning Life Sciences, Corning, N.Y.). Multi-well plates are preferably made of a material that sufficiently adheres the brain extract components such that the subsequent steps (washing and incubation) of a solid phase binding assay can be carried out. For example, polystyrene multi-well plates optionally coated with additional functional groups, including ionic groups, maleimide groups, or hydrazide groups are of use in the identification assays of the present invention.

Once the separated brain extract components are sufficiently adhered to a substrate of choice, they are exposed to a sample from an individual. The sample is diluted in an appropriate biological buffer before contacting it with brain extract components, usually about 1:100, 1:250, 1:500, 1:750, 1:1000, 1:2000 or more if necessary. If appropriate, a sample can be used in the present assays without dilution (neat) or with minimal dilution, for example, about 1:2, 1:5, 1:10, 1:50. The amount of dilution is not critical to the success of the invention so long as sufficient sensitivity is realized with out a loss of resolution due to overexposure resulting from an overload of sample.

A sample is incubated with separated brain extract components under conditions (i.e., time, temperature, concentration of sample) sufficient to allow specific binding of any antibodies or autoantibodies present in the sample. For example, brain extract components can be exposed to a sample for about 0.5, 1.0, 1.5, 2.0, 2.5, 3.0 hours, or overnight, about 8, 10 or 12 hours. However, incubation time can be more or less depending on the dilution of the sample and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

Labeled secondary antibodies are generally used to detect antibodies or autoantibodies in a sample that have bound to one or more brain extract components (i.e., neural antigens). Secondary antibodies bind to the constant or "C" regions of different classes or isotypes of immunoglobulins—IgM, IgD, IgG, IgA, and IgE. Usually, a secondary antibody against a IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (i.e., fluoroscein, phycoerythrin), an enzyme (i.e., peroxidase, alkaline phosphatase), a radioisotope (i.e., $^3H$, $^{32}P$, $^{125}I$) or a chemiluminescent moiety. Labeling signals can be amplified using a complex of biotin and a biotin binding moiety (i.e., avidin, streptavidin, neutravidin). Fluorescently labeled anti-human IgG antibodies are commercially available from Molecular Probes, Eugene, Oreg. Enzyme-labeled anti-human IgG antibodies are commercially available from Sigma-Aldrich, St. Louis, Mo. and Chemicon, Temecula, Calif.

The method of detection of the presence or absence, or differential presence, of antibodies or autoantibodies in a sample will correspond with the choice of label of the secondary antibody. For example, if the separated brain extract components are transferred onto a membrane substrate suitable for immunoblotting, the detectable signals (i.e., blots) can be quantified using a digital imager if enzymatic labeling is used or an x-ray film developer if radioisotope labeling is used. In another example, if the separated brain extract components are transferred to a multi-well plate, the detectable signals can be quantified using an automated plate reader capable of detecting and quantifying fluorescent, chemiluminescent, and/or calorimetric signals. Such methods of detection are well known in the art.

General immunoassay techniques are well known in the art. Guidance for optimization of parameters can be found in, for example, Wu, *Quantitative Immunoassay: A Practical Guide for Assay Establishment, Troubleshooting, and Clinical Application,* 2000, AACC Press; *Principles and Practice of Immunoassay,* Price and Newman, eds., 1997, Groves Dictionaries, Inc.; *The Immunoassay Handbook,* Wild, ed., 2005, Elsevier Science Ltd.; Ghindilis, Pavlov and Atanassov, *Immunoassay Methods and Protocols,* 2003, Humana Press; Harlow and Lane, *Using Antibodies: A Laboratory Manual,* 1998, Cold Spring Harbor Laboratory Press; and *Immunoassay Automation: An Updated Guide to Systems,* Chan, ed., 1996, Academic Press.

The presence or differential presence of one or more (auto) antibodies indicative of a neurodevelopmental disorder or indicative of the risk of developing a neurodevelomental disorder, including an autism spectrum disorder, is indicated by the presence, or a differential greater presence, of a detectable signal (i.e., a blot, fluorescence, chemiluminescence, color, radioactivity) in a brain extract immunoassay, where the brain extract is contacted with a sample from an individual with a neurodevelopmental disorder or with antibodies against one or more neural antigens. This detectable signal is compared to the absence, or a differential diminished presence, of a detectable signal from the same brain extract component in a brain extract immunoassay control, where the brain extract is contacted with a sample from an individual without a neurodevelopmental disorder or without antibodies against neural antigens. A differential presence is detected when the detectable signal is about 10%, 20%, 30%, 50%, 75% greater in comparison to a control when the brain extract is contacted with a sample from an individual with a neurodevelopmental disorder, including an ASD, or with antibodies against one or more neural antigen. A differential presence is detected when the detectable signal is about 1-fold, 2-fold, 3-fold, 4-fold or more, greater in comparison to a control.

In carrying out the step of detecting a pattern of staining of brain regions and cell types bound by an antibody or autoantibody in a sample, the sample from an individual (i.e., a patient or a potential mother) is contacted with an intact brain section. Similar to the preparation of a brain extract, an in situ brain section is usually from a non-human primate, a human cadaver, a human fetus, or a non-human primate fetus. In certain instances, it is appropriate to use a brain section from a mammal, for example, from a pig, dog, cat, rat, or mouse. A brain section can be prepared from a whole brain, including portions of the spinal cord, or can be from specific brain regions or subregions. For example, a brain section can be prepared from one or more brain regions including, for example, right or left cerebral hemispheres, frontal, parietal, temporal, or occipital lobes and brain stem. Brain sections can also be prepared from one or more specific subregions of the brain, including, for example, the cerebellum, hypothalamus, dorsal thalamus, hippocampus, amygdala, cerebral cortex, orbitofrontal cortex, neocortex, medulla, midbrain, pons, and spinal cord. Depending on the particular pattern to be identified, a brain section can be a coronal, a horizontal or a sagittal section.

Brain sections are then contacted with a sample from an individual, diluted as described above, and exposed to the sample under conditions allowing any antibodies or autoantibodies present to specifically bind to one or more neural antigens in the brain section. Incubation parameters, including time, temperature and concentration of sample, can be adjusted as described above. Washing to remove unbound sample before addition of a secondary antibody is carried according to known immunohistochemistry methods. Labeled secondary antibodies against the constant regions of the antibodies or autoantibodies, as described above, are used to detect the presence of the antibodies or autoantibodies that specifically bind one or more neural antigens, or their differential presence, and the particular cell types and brain localities to which they bind. The labels on the secondary antibodies for detecting binding of antibodies or autoantibodies to brain sections should be appropriate to well known methods of immunohistochemistry, for example, a fluorophore (i.e., fluoroscein isothiocyanate), an enzyme (i.e., peroxidase, alkaline phosphatase), a chromophore (i.e., 3,3'-diaminobenzidine-tetrahydrochloride-dihydrate (DAB)). Labeling signals can be amplified using a complex of biotin and a biotin binding moiety (i.e., avidin, streptavidin, neutravidin). Guidance for optimization of immunohistochemistry parameters can be found, for example, in Dabbs, *Diagnostic Immunohistochemistry*, 2001, Elsevier Science Health Science Division.; *Immunohistochemistry II*, Cuello, ed., 1993, John Wiley & Sons; and Shi, et al., *Antigen Retrieval Techniques: Immunohistochemistry and Molecular Morphology*, 2000, Eaton Publishers. Kits for immunohistochemistry methods are commercially available from, for example, Vector Laboratories, Burlingame, Calif.; ResGen, through Invitrogen, Carlsbad, Calif.; and BioCat, Heidelberg, Germany.

An immunohistochemical staining pattern indicative of a neurodevelopmental disorder in an individual or indicative of risk of development of a neurodevelopmental disorder in a potential fetus can be identified by visual inspection, for instance using an appropriate microscope to detect the labeled secondary antibodies. A staining pattern indicative of a neurodevelopmental disorder, including an ASD, is identified when a unique staining pattern is observed in a brain section contacted with a sample from an individual with a known neurodevelopmental disorder and not observed in the same brain section contacted with a sample from an individual who does not have a neurodevelopmental disorder. A staining pattern indicative of a risk of developing a neurodevelopmental disorder, including an ASD, is identified when a unique staining pattern is observed in a brain section contacted with a sample from an individual having antibodies against one or more neural antigens and not observed in a corresponding brain section contacted with a sample from an individual who does not have antibodies against one or more neural antigens.

To provide a non-limiting example, a staining pattern of scattered intensively stained cells just below the Purkinje layer of the cerebellum (the granular layer) is observed in brain sections contacted with serum from individuals having an ASD, but not in brain sections from individuals not having an ASD. The staining is intracytoplasmic and stains the length of the dendrites. By contrast, a staining pattern of the neocortex in general is indicative of mental retardation or learning disabilities. A staining pattern also can be defined by the types of cells that appear stained (i.e., cells of the granular layer, Golgi Type II cells, brain endothelial cells), or by particular proteins bound by (auto)antibodies in the samples (i.e., neuron-axon filament protein (NAFP), cerebellar neurofilaments, myelin basic protein).

A staining pattern can also be used to distinguish an ASD from other neurodevelopmental disorders. A staining pattern indicative of an ASD, as distinguished from a different neurodevelopmental disorder, is identified when a unique staining pattern is observed in a brain section contacted with a sample from an individual with an ASD and not observed in a corresponding brain section contacted with a sample from an individual who does not have an ASD but has a different neurodevelopmental disorder. Likewise, a brain section staining pattern can be used to distinguish high functioning autism from low functioning autism.

Methods of Diagnosis

The invention further provides for methods of diagnosing a neurodevelopmental disorder, including an ASD, in an individual, the method comprising determining the presence or absence, or differential presence, of an autoantibody in a sample from the individual, wherein the autoantibody is directed against a neural antigen located in one or more regions of the brain selected from the group consisting of the cerebellum, the hypothalamus, the amygdala and the orbitofrontal cortex, wherein the presence of the autoantibody indicates that the individual has a neurodevelopmental disorder, and wherein the autoantibody was previously identified according the methods described herein.

The invention further provides for methods of diagnosing the risk of developing a neurodevelopmental disorder, including an ASD, in a mother's future offspring, the method comprising determining the presence or absence, or differential presence, of an antibody in a sample from the mother, wherein the antibody is directed against a neural antigen located in one or more regions of the brain selected from the group consisting of the cerebellum, the hypothalamus, the amygdala and the orbitofrontal cortex, wherein the presence of the antibody indicates that the individual has a neurodevelopmental disorder, and wherein the antibody was previously identified according the methods described herein. Typically, the neural antigen is a fetal neural antigen.

The methods of diagnosis can be carried out according to the 2-prong process described above. A sample from an individual (i.e., a patient or a potential mother) are contacted with separated components of a brain extract, as described above, and the binding of one or more (auto)antibodies in the sample to one or more components in the brain extract are evaluated by immunoassay. The sample is further contacted with a brain section and the binding of one or more (auto)antibodies in the sample to one or more components in the brain section are evaluated by immunohistochemistry.

In one embodiment, the methods of diagnosis of a neurodevelopmental disorder can be carried out using either immunoassay or immunohistochemistry. In one embodiment, the methods of determining the risk that a mother's future offspring will have a neurodevelopmental disorder can be carried out using either immunoassay or immunohistochemistry. Specific biomarkers indicative of a neurodevelopmental disease mediated by an (auto)antibody neural tissue destruction, including an ASD, can be detected for diagnosis by contacting a sample from an individual with a brain extract, as described above. Unique staining patterns in an in situ brain section can be detected for diagnosis by contacting a sample from an individual with a brain section, as described above.

A diagnosis of a neurodevelopmental disorder is indicated with the determination of the presence, or differential presence, in a sample from an individual of an (auto)antibody that specifically binds to a neural antigen located in one or more regions of the brain, including the cerebellum, the hypothalamus, the amygdala and the orbitofrontal cortex. Where a diagnosis is indicated, a detectable signal of one or more components in a brain extract bound to an (auto)antibody is identified when contacted with a sample from an individual having a neurodevelopmental disorder, including an ASD; the detectable signal of the same components is not detected in brain extracts contacted with a sample from an individual not having a neurodevelopmental disorder, or not having an ASD. Further, a diagnosis of a neurodevelopmental disorder, including an ASD, is indicated when a detectable pattern of staining of a brain section is identified when a brain section is contacted with a sample from an individual having a neurodevelopmental disorder, including an ASD; the detectable pattern of staining of the same brain section is not detected when contacted with a sample from an individual not having a neurodevelopmental disorder, or not having an ASD.

When one or more identifying components indicative of a neurodevelopmental disorder from brain extracts are identified, or when unique staining patterns indicative of a neurodevelopmental disorder, including an ASD, are identified, a diagnosis or determination of risk can be established without comparing each replicate to a control (i.e., a sample from an individual who does not have a neurodevelopmetal disorder, including an ASD, or a sample from an individual who has a different neurodevelopmental disorder). To provide a non-limiting example, a staining pattern of scattered intensively stained cells just below the Purkinje layer of the cerebellum (the granular layer) is observed in brain sections contacted with serum from individuals having an ASD, but not in brain sections from individuals not having an ASD. The staining is intracytoplasmic and stains the length of the dendrites. By contrast, a staining pattern of the neocortex in general is indicative of mental retardation or learning disabilities. A staining pattern also can be defined by the types of cells that appear stained (i.e., cells of the granular layer, Golgi Type II cells, brain endothelial cells), or by particular proteins bound by (auto)antibodies in the samples (i.e., neuron-axon filament protein (NAFP), cerebellar neurofillaments, myelin basic protein).

Primate Model for Evaluating Neurodevelopmental Disorders

The invention further provides methods for evaluating the etiologies and pathological processes of a neurodevelopmental disorder, including an autism spectrum disorder, the methods generally comprising fetal exposure of a subject primate to a putative or known causative factor for the neurodevelopmental disorder and then evaluating psychological, social, cognitive and physiological development of the subject primate throughout its entire lifespan or over continuous or discontinuous time periods of its lifespan.

Accordingly, the invention provides methods for determining the pathological process(es) of a neurodevelopmental disorder, including an autism spectrum disorder, comprising:
 a) exposing a non-human primate fetus to a known causative factor of the neurodevelopmental disorder;
 b) after birth and up until weaning, raising the infant subject primate with its mother and a primate social group comprising at least two other mother-infant primate pairs and at least one male primate;
 c) following weaning, determining at least one developmental indicator selected from the group consisting of neurological status, social performance, emotional performance, behavioral performance and cognitive performance.

The invention further provides methods for determining the causative factor(s) of a neurodevelopmental disorder, including an autism spectrum disorder, comprising:
 a) exposing a non-human primate fetus to a putative or suspected causative factor of a neurodevelopmental disorder;
 b) after birth and up until weaning, raising the infant subject primate with its mother and a primate social group comprising at least two other mother-infant primate pairs and at least one male primate;
 c) following weaning, determining at least one developmental indicator selected from the group consisting of neurological status, social performance, emotional performance, behavioral performance and cognitive performance.

In some embodiments, the subject primate is compared to a control primate that was not exposed to the known or putative causative factor. Typically, the subject primate and the control primate are age-matched. The subject primates can be evaluated for a discrete time period (e.g., as infants, as juveniles and/or as adults), for one or more continuous or discontinuous time periods, or from birth to death, as desired or necessary.

The causative factors can be chemical, physical or environmental. For example, the causative factor can be an (auto) antibody specific for a neural antigen, as described herein. Exposure to the causative factor can be for the full gestational period of the fetus or only for a portion of the gestational period. For example, exposure can be throughout a first or second half of the gestational period, or throughout the first, second or third trimester of the gestational period. Exposure to the causative factor can be one or more times during the gestational period, for example, on one or more particular days of gestation. In some embodiment, exposure of the mother to the causative factor can begin before conception and pregnancy. In some embodiments, the causative factor is delivered to the pregnant mother orally or parentarelly (e.g., intravenously, subcutaneously, intra-uterine). In some embodiments, the causative factor is delivered directly to the fetus, to the directly surrounding environment of the fetus (e.g., to the amniotic sac), or to the placenta.

In some embodiments, the subject primate is a Rhesus monkey (*Macaca mulatta*) but any other non-human primate exhibiting evaluative social, emotional, behavioral and/or cognitive performances can be used in the model.

The social groups can comprise the subject primate and its mother (dyad interactions), between the subject primate and its mother and one other mother-infant pair (tetrad interactions), or at least two other mother-infant pairs, and at least one adult male (social group interactions). The size of the social group can be adjusted based on the tests to be administered and the study design. Typically the size of the social group will about 10, 12, 15, 18, 20 or more primates. In some embodiments, the social group can comprise up to ten other mother-infant pairs, for example, about 2, 3, 4, 5, 6, 7, 8, 9, 10 mother-infant pairs. In some embodiments, the social group comprises more than one adult male, for example, 2, 3, 4 or 5 males. Usually, a social group will comprise a greater number of adult females (i.e., mothers) than adult males.

Social, emotional, behavioral or cognitive performances can include evaluating one or more parameters including physical behaviors, degree of social interest, degree of social fear or fear in general, memory ability, learning ability, degree of focused attention ability, responsiveness towards others inside and outside the social group, responsiveness towards familiar or novel situations or objects. For example, primate fetuses exposed to a causative factor of an autism spectrum disorder can exhibit one or more of decreased social interest, increased social fear, increased stereotypical physical behaviors, decreased memory ability, decreased focused attention, decreased responsiveness towards others (e.g., its mother, others within its social group, others outside of its social group). Specific tests can be developed based on psychological, physiological, sociological and cognitive tests known in the art.

For physiological testing, for example, brain scans can be taken using magnetic resonance imaging (MRI). Primates are anesthetized and then placed in an MRI-compatible sterotaxic apparatus (available from Crist Instruments, Damascus, Md.). The brain can be imaged using a 1.5 T Gyroscan magnet (General Electric, Waukesha, Wis.). The brain can be imaged in coronal, horizontal and/or sagittal sections from about 1.0 mm to about 1.5 mm using techniques known in the art. See, Bauman, et al., *J Neurosci* (2004) 24:711; Shamy, et al., *Neurobiol Aging* (2005) PMID:16183171, in press.; Huettel, et al., *Functional Magnetic Resonance Imaging,* 2005, Sinauer Associates; and Haacke, et al., *Magnetic Resonance Imaging: Physical Principles and Sequence Design,* 1999, Wiley-Liss. Different areas of the brain can be quantified, for example, the volume of hippocampus, amygdala, cerebral, ventricular areas can be determined. The scans are evaluated for developmental differences between a primate that has been subject to a causative factor and a control that has not.

For testing the social and/or emotional performance of a subject primate, tests can include evaluating mother-infant contact time; preference of a weaned child for its mother; the type, frequency and duration of vocalizations; and type, frequency and duration of behaviors in general, as described below. See, Bauman, et al., *J Neurosci* (2004) 24:711. Responsiveness or non-responsiveness, indicative of fear, anxiety, increased or decreased inhibitions, increased or decreased interest, can be tested, for example, by exposing the subject primate to a familiar or novel object (e.g., a favored toy, a metal object, toy animals, including replicas of a natural predator) or a familiar or novel situation (e.g., exposure to a familiar non-human primate (e.g., conspecific), exposure to an unfamiliar non-human primate (e.g., conspecific), exposure to an unfamiliar human). See, Mason, et al., *Emotion* (2006) 6:73-81; Bauman, *J Cogn Neurosci* (2004) 16:1388 and Prather, et al., *Neurosci* (2001) 106:653.

Cognitive performance, including learning and memory ability, can be tested, for example, using a delayed non-matching-to-sample (DNMS) test. Briefly, DNMS trials are initiated by presenting a sample object over a baited central well of a manual test apparatus. After a predetermined interval, during which the stimuli are hidden from view, the sample object is presented with a novel stimulus that covers a reward. Trial-unique pairs of objects are used across trials and the rewarded item appears equally often over the left and right wells of the testing apparatus. Once the non-matching rule of the task is learned, testing is made to require successively increasing retention intervals, for example, increasing from 10 seconds to 600 seconds or more. See, Shamy, et al., *Neurobiol Aging* (2005) PMID:16183171, in press; Rapp and Amaral, *J Neurosci* (1989) 9:3568; Rapp and Amaral, *Neurobiol Aging* (1991) 12:481 and Rapp, et al., *J Neurosci* (2003) 23:5708.

In some embodiments, the subject primate is evaluated by placing it in different social contexts, for example, by placing it in an enclosure with its mother, with one or more primates from within its social group, or with one or more primates from outside its social group.

In one embodiment, the physical behaviors of the subject primate are evaluated in different social contexts. The type (e.g., stereotypical behaviors including pacing, twirling, back-flipping, swinging and other behaviors described below), frequency and duration of the physical behaviors are recorded.

Behavioral data can be collected using The Observer software (Noldus, Sterling, Va.) (Noldus, 1991) or another appropriate software program. Recordations are entered by trained observers demonstrating an interobserver reliability of at least 90% [agreements/(agreements+disagreements)× 100%]. Observers remain blind to the treatment of the subject primate. Recordations can include whether a certain behavior occurs (one-zero behavior scoring), or the type, duration and frequency that a certain behavior occurs. Behaviors are typically recorded during "focal sample" periods, that can last, for example, for any defined amount of time from 10 seconds to 5 minutes, or longer or shorter, as desired. Behaviors can be recorded if the subject primate is initiating or responding.

Behaviors are generally recorded based on a catalog of commonly observed activities for the primate species, including without limitation, nursing, playing, grooming, social interaction, sleeping, touching, clasping, hitting, biting, grabbing, slapping, aggression, anogenital exploration, oral exploration, manual exploration, cage shaking, chasing, fleeing, following, freezing, mounting, no contact, nonsocial activity, vocalizations, (e.g., barking, cooing, grunting, lipsmacking, screaming, tantrum), non-verbal expressions (e.g., crook tail, fear grimace, proximity to another, approaching another, scratching, threatening, withdrawing, yawning, detachment), etc. See, for example, Bauman, et al., *J Neurosci* (2004) 24:711.

Comparisons between subject primates exposed to a causative factor of a neurodevelopmental disorder and control primates not exposed to a causative factor can be statistically analyzed. For statistical analysis, The Statistical Program for the Social Sciences (version 14.0; SPSS, Chicago, Ill.) or other appropriate software can be used. To compare behavioral data between groups and test days, a two-way repeated-measures ANOVA or ANCOVAs can be used for parametric analysis. In appropriate cases, paired t tests are performed. Guidance for the application of statistics can be found, for example, Thomson Learning; Gravetter and Wallnau, *Statistics for the Behavioral Sciences,* 2003, Thomson Learning; Samuels, et al., *Statistics for the Life Sciences,* 2002, Prentice Hall; and Tabachnick and Fidell, *Using Multivariate Statistics,* 2001, Allyn and Bacon.

EXAMPLES

The following examples are offered to illustrate, but not to limit the claimed invention.

Example 1

This example describes identifying autoantibodies against neural antigens and the local brain regions bound by such autoantibodies.

Serum or plasma from the patient with ASD is separated from the cell pellet and diluted 1:250, 1:500 and 1:1000. Human brain extracts (BD Biosciences/Clontech, Inc.) from various regions of the brain are separated by SDS-PAGE gel electrophoresis in a 12% gel under reducing conditions at a concentration of 15 μg/lane. The gel is blotted onto nitrocellulose overnight and washed in PBS. 4 mm strips are cut and placed into a tray with individual wells. The strips are blocked with 3% milk-PBS for 20 min. The diluted serum or plasma is then added for a 2 hour incubation, then the strips are washed 5× in PBS-tween. Following the washing procedure, the strips are incubated with a goat-anti-human IgG peroxidase conjugate for 1 hour, washed 5× with PBS-Tween and incubated with a chemiluminescence detection reagent for 5-15 min. The blots are imaged on an Alphalnnotech imager. The Rf and density of each band is determined using the Alphalnnotech software.

The sensitivity of this assay is increased by reacting autoantibodies with tissue sections from nonhuman primate brains using standard immunohistochemical techniques, for example the following protocol and conditions can be used.

Day 1:
All washing and incubation at room temp with rotation unless indicated.
Tissue from tissue culture solution (TCS) is washed 3×10 min in 0.1M phosphate buffered saline (PBS)
Hydrogen peroxide pretreatment: 1.65 ml $H_2O_2$ in 100 ml PBS
 15 minutes
Tissue washed in PBS 3×10 min., 1×20 min, blot.
For 25 ml (per base)
Blocking (4 hours)
 0.1M PBS
  0.5% Triton X-100
  5% Normal Mouse Serum (NMS)
 blot
Primary antibody incubation (40-48 hours at 4 degrees C.)
 0.1M PBS
 0.3% Triton X-100
 2% NMS
 Primary antibody
Day 3:
Wash in PBS with 2% normal goat serum (NGS) 3×10 min.
Blot
1st incubation with secondary antibody (1 hr)-cover and save for re-use
 0.1M PBS
 0.3% Triton X-10
 2% NMS
 secondary antibody-biotin conjugated mouse anti-human IgG
Wash in PBS with 2% NGS 3×10 min
Blot
1st incubation with Avidin-Biotin-Peroxidase complex (ABC) (45 min)-cover and save for
re-use
Wash in PBS with 2% NGS 3×10 min.
Blot
2nd incubation with secondary antibody (45 min)
In a clean Petri dish wash with PBS with 2% NGS 3×10 min
2nd incubation with ABC-Peroxidase complex for 30 min.
Wash in 0.05M Tris 3×10 min
Blot
DAB Incubation-30 min-prepared immediately prior to use
 0.05% 3,3'-diaminobenzidine-tetrahydrochloride-dihydrate (DAB)
 0.04% hydrogen peroxide in 0.1M Tris
Wash in 0.1M Tris 2×10 min
Wash in PBS 1×10 min
Sections mounted and dried at 37 degrees C. at least, overnight.
Intensification and coverslipping should be done within a week.
 Silver Nitrate and Gold Chloride Intensification of DAB immunohistochemistry
Acid clean staining dishes, stir bar and Ehrlenmeyer flask overnight.
Use MilliQue water for silver nitrate and gold chloride solutions.
*Silver nitrate and gold chloride are both light-sensitive, so care is taken in protecting them from extended exposure.
Defat slides in mixture of equal part chloroform: 100% ethanol, 2 hours with "once used" solution plus 2 hours with fresh solution.
Hydrate through graded ethanols: 2 minutes each in 100%, 100%, 95%.
Slides dried at 37 degrees C. overnight.
Slides rinsed in running $dH_2O$ for 10 min.
Equilibrate and maintain 1% silver nitrate solution at 56 degrees C. and incubate slides in it for 40 min in a covered waterbath. Protect from light. Clean up all spills immediately.
Rinse slides in running $dH_2O$ 10 min.
Incubate for 10 min. in 0.2% gold chloride at room temperature in dark.
Solution may be reused up to 2 more times during the same experiment. Agitate slide racks occasionally during incubation.
Rinse slides in running $dH_2O$ for 10 min.
Stabilize in 5% sodium thiosulfate at room temperature with occasional agitation for 15 min.
Rinse in running $dH_2O$ for 10 min.
Dehydrate through graded ethanols. 4 min each in 50%, 70%, 95%, 200%, 100%, 1st xylene, 2nd xylene, 3rd xylene and coverslip using DPX.

A pattern of regional or cellular labeling that is observed. Antibodies directed at the cerebellum, amygdala or orbitofrontal cortex are associated with autism whereas antibodies directed at the neocortex in general are associated with mental retardation or learning disabilities. By identifying the presence of autoantibodies against neural antigens and the regions of the brain to which the autoantibodies bind, a correlation between immunoblotting and immunohistochemical labeling with a risk of a neurodevelopmental disorder, including an ASD, is established.

Example 2

This example describes identifying maternal antibodies against fetal neural antigens and the local brain regions bound by such antibodies.

Serum or plasma from the mother is separated from the cell pellet and diluted 1:250, 1:500 and 1:1000. Fetal brain extract (BD Biosciences/Clontech, Inc.) is separated by SDS-PAGE gel electrophoresis in a 4-20% gradient gel under reducing conditions at a concentration of 15 μg/lane. The gel is blotted onto nitrocellulose overnight and washed in PBS. 4 mm strips are cut and placed into a tray with individual wells. The strips are blocked with 3% milk-PBS for 20 min. The diluted serum or plasma is then added for a 2 hour incubation, then the strips are washed 5× in PBS-tween. Following the washing procedure, the strips are incubated with a goat-anti-human IgG peroxidase conjugate for 1 hour, washed 5× with PBS-Tween and incubated with a chemiluminescence detection reagent for 5-15 min. The blots are imaged on an Alphalnnotech imager. The Rf and density of each band is determined using the Alphalnnotech software.

The sensitivity of this assay is increased by reacting antibodies in mothers' blood with tissue sections from nonhuman primate brains using standard immunohistochemcal techniques (exemplified above). A pattern of regional or cellular labeling is observed. Antibodies directed at the cerebellum, amygdala or orbitofrontal cortex are associated with autism whereas antibodies directed at the neocortex in general are associated with mental retardation or learning disabilities. By identifying the presence of maternal antibodies against fetal neural antigens and the regions of the brain to which the maternal antibodies bind, a correlation between immunoblotting and immunohistochemical labeling with a risk of a neurodevelopmental disorder, including an ASD, is established.

Example 3

This example demonstrates the development of autistic-like behaviors in primate offspring exposed during gestation to human maternal IgG collected from sera of mothers of at least two children with an ASD.

Rationale and Study Design

The rhesus monkey was used as a model for the study of autism because it has several specific advantages over other animal model systems. In particular, the social repertoire of monkeys is much broader than that of rodents, making it useful for the analysis of normal and pathological human social behavior (Deaner, et al., *Curr Biol* (2003) 13:1609 and Gothard, et al., *Anim Cogn* (2004) 7:25). We have developed an extensive battery of behavioral tests aimed at exploring the neural basis of social behavior in rhesus monkeys. This battery involves testing during highly controlled social interactions using a comprehensive and well-defined ethogram (catalogue of species-typical behaviors) to quantitatively assess behavior. This testing battery is very sensitive at detecting subtle deficits in social behavior including increased affiliative behavior in adult monkeys with bilateral lesions of the amygdala and increased fear responses in infant monkeys with bilateral lesions of the amygdala during novel dyadic social interactions (Emery, et al., *Behav Neurosci* (2001) 115:515; Bauman, et al., *J Cogn Neurosci* (2004) 16:1388; Bauman, et al., *J Neurosci* (2004) 24:711).

Materials and Methods

Antibody Acquisition and Preparation

Human Sera from 21 mothers of at least one child with autism and one or more additional children with autism spectrum disorders were purchased from the Autism Genetic Resource Exchange (AGRE). Human sera from 7 mothers of multiple typically developing children were collected locally. In both cases, the protocol for obtaining blood samples was approved by an appropriate Internal Review Board (IRB).

Western Blots

All serum samples were screened for the presence of antibodies directed against brain tissue using western blots. Human fetal brain protein medley (300 µg; Clontech Laboratories, Mountain View, Calif.) was separated on a 4-15% gradient reducing gel using SDS-PAGE electrophoresis and transferred onto nitrocellulose paper. Antibody reactivity to the fetal brain extracts was then analyzed for all samples individually by Western blotting. The blots were incubated for 3 hours in a 0.1 M phosphate buffered saline (PBS, pH 7.4) solution containing serum from the above samples at a dilution of 1:400, with 5% milk and 0.3% Triton X-100. Following a series of rinses, the extracts were incubated for 1 hr with a goat anti-human IgG peroxidase-conjugated antibody and visualized using chemiluminescence in a Fluorchem 8900 imager (Alpha Innotech, San Leandro, Calif.). The maternal autism serum samples were then separated into 2 groups based upon similar banding patterns within each group (designated banding pattern A and banding pattern B in FIG. 1).

Purification of IgG Antibodies

The pooled sera with banding pattern A or banding pattern B was diluted with Immunopure (G) IgG binding buffer (Pierce Biotechnology, Inc, Rockford, Ill.) and IgG antibodies were purified on Ultralink Affinity Pack immobilized protein G columns (Pierce Biotechnology, Inc, Rockford, Ill.). Purified IgG was then eluted from columns with Immunopure IgG elution buffer (Pierce Biotechnology, Inc, Rockford, Ill.). This process resulted in approximately 3.3 mg of purified IgG per 1 ml serum. The purified serum was screened for the presence of HIV and Hepatitis B and C and finally sterile filtered with a 0.2 µm filter prior to injection.

Subjects and Living Conditions

All procedures carried out on animal subjects were approved by the UC Davis Institutional Animal Use and Care Committee. The subjects for this study were thirteen naturally born rhesus monkeys (Macaca mulatta). The mothers of the subjects were randomly assigned to one of three treatment conditions. Four mothers were exposed during pregnancy to human IgG antibodies (banding pattern A) from mothers of multiple children with ASD. Four other mothers were exposed during pregnancy to human IgG from mothers of multiple typically developing children. In all cases, 15-20 mg of purified IgG diluted in 5 ml of sterile saline was delivered intravenously on three separate occasions: days 27, 41, and 55 of gestation. The final five mothers were left untreated. All infants were born and raised in standard home cages (61×66× 81 cm). Each mother-infant pair was assigned to a socialization group consisting of six mother-infant pairs and one adult male. There were two male and four female infants in each group.

In addition to the thirteen monkeys in this study, the socialization groups included 2 mother-infant pairs from an additional treatment group exposed to maternal autism IgG and 3 mother-infant pairs from a simulated phenylketonuria (PKU) treatment condition. The IgG (banding pattern B in FIG. 1) given to this additional maternal autism IgG treated group differed from the IgG (banding pattern A) given to the maternal autism IgG treated mother-infant pairs in this study. The group receiving IgG from banding pattern B mothers was originally designed to also have 4 mother-infant pairs, but 2 fetuses did not come to term due to typical rhesus monkey pregnancy complications. Given the small number of remaining infants in this group, they were not included in this study.

The composition of the socialization groups was as follows: Groups 1 and 2 consisted of 1 PKU mother-infant pair, 2 maternal autism IgG treated mother-infant pairs (1 IgG banding pattern A and 1 IgG banding pattern B), and 3 control mother-infant pairs (1 IgG and 2 untreated controls). Group 3 consisted of 1 PKU mother-infant pair, 2 maternal autism IgG treated mother-infant pairs (both IgG banding pattern A), and 3 control mother-infant pairs (1 untreated and 2 IgG controls).

When the youngest subject within each socialization group reached approximately 6 months of age, all of the infants within that group were permanently separated from their mothers (weaned), a common animal husbandry practice at the primate center, and moved to large group cages (2.13× 3.35×2.44 m). The adult males remained with each group and a novel adult female was added to each group for a period of 1 month following weaning to provide group stability.

Behavioral Observations

Mother Preference Test

On the first 4 days immediately following weaning, each infant was observed in a test designed to evaluate one aspect of mother-infant attachment, the infant's preference for its mother over another familiar adult female. Five daily 2 min trials were conducted, with each trial consisting of a choice between the infant's mother and one of the five other adult females from the infant's socialization group (the stimulus female). A different stimulus female was used for each trial in a predetermined pseudorandom order. Before each trial, the test subject was hand-caught by a technician and placed in a plastic release box in the center of an unfamiliar chain link testing enclosure (5.56×1.91×2.13 m). The front of the subject's release box was transparent and the remaining three sides were opaque allowing the test subject to view only the observers until released. The subject's mother was placed in one of two holding cages, located at either end of the testing enclosure, and the stimulus female was placed in the opposite holding cage (holding cage assignments were balanced across trials). Transparent plastic panels prevented physical contact between the test subject and the adult females. Opaque plastic panels in front of the holding cages prevented the adult females from seeing the release box before testing.

At the onset of the trial, the subject's release box and the opaque panels in front of the holding cages were raised simultaneously, allowing the test subject to freely move around the testing enclosure and see both its mother and the stimulus female. During each 2 min trial, trained observers recorded which adult was first approached by the test subject (scored when the subject moved within a 1 meter half-circle painted on the floor in front of each holding cage), the spatial location of the subject every 15 sec (three-dimensional space was determined using a floor grid of 9×3 quadrants-0.61×0.64 m-, and 2 evenly spaced horizontal bars dividing the vertical dimension into 3 sections), and behaviors exhibited by the test subject (scored from a list of predetermined normal and abnormal rhesus monkey behaviors).

Solo and Familiar Dyad Observations

One month following weaning (when the animals were on average 8.5 months old), each subject was observed in a test setting designed to study the behavior of the subject alone and during interactions with familiar peers. Subjects were removed from their socialization groups and placed in individual holding cages. Each subject was then placed alone in a large testing enclosure similar to their home environment and observed for two consecutive 5 min sessions. Immediately following these initial solo observations, the first day of familiar social dyad observations began. Subjects were placed into the testing enclosures in pairs to form social dyads. Each social dyad consisted of two subjects from the same socialization group. Social dyads were 20 min in duration with the focal subject alternating every 5 min. Each subject met with each other subject in their socialization group on two occasions separated by at least one day. Social dyads were spread out over 5 consecutive testing days with each subject participating in 2 separate 20 min dyads each day in a predetermined pseudo-random order. On the final day of familiar social dyad testing, each subject was again observed alone for two consecutive 5 min sessions. For each observation, solo or dyad, trained observers used the Noldus Observer software program on laptop computers to score the behavior of each focal subject from a behavioral ethogram of normal and abnormal rhesus monkey behaviors.

Unfamiliar Dyad Observations

One month following the solo and familiar dyad observations (when the animals were on average 9.5 months old), each subject was observed in a test setting designed to study the behavior of the subject during interactions with unfamiliar peers. Four age-appropriate stimulus monkeys (2 males and 2 females) were temporarily added to the project to serve as unfamiliar peers. Subjects were again removed from their socialization groups and placed in individual holding cages. Subjects were then paired with one of the four unfamiliar peers in the same testing enclosures used for solo and familiar dyad observations. These unfamiliar dyads were also 20 min in duration with the focal subject alternating every 5 min. Each subject met with each of the unfamiliar peers on two occasions separated by at least one day. The unfamiliar social dyads were therefore spread out over 4 consecutive testing days, with each subject participating in 2 separate 20 min dyads each day, again in a predetermined pseudorandom order. Behavioral scoring was similar to the other observations.

Social Group Observations

In addition to the acquisition of behavioral data in novel testing environments, each subject was also observed within their socialization groups in their home cage environment. Each subject was observed for 5 min twice per week, only during weeks in which no other testing took place. A total of 30 observations were conducted on each subject, with all testing taking place in the weeks following the unfamiliar dyads. Behavioral scoring was again similar to the previous observations.

Statistical Analyses

Figure 2:
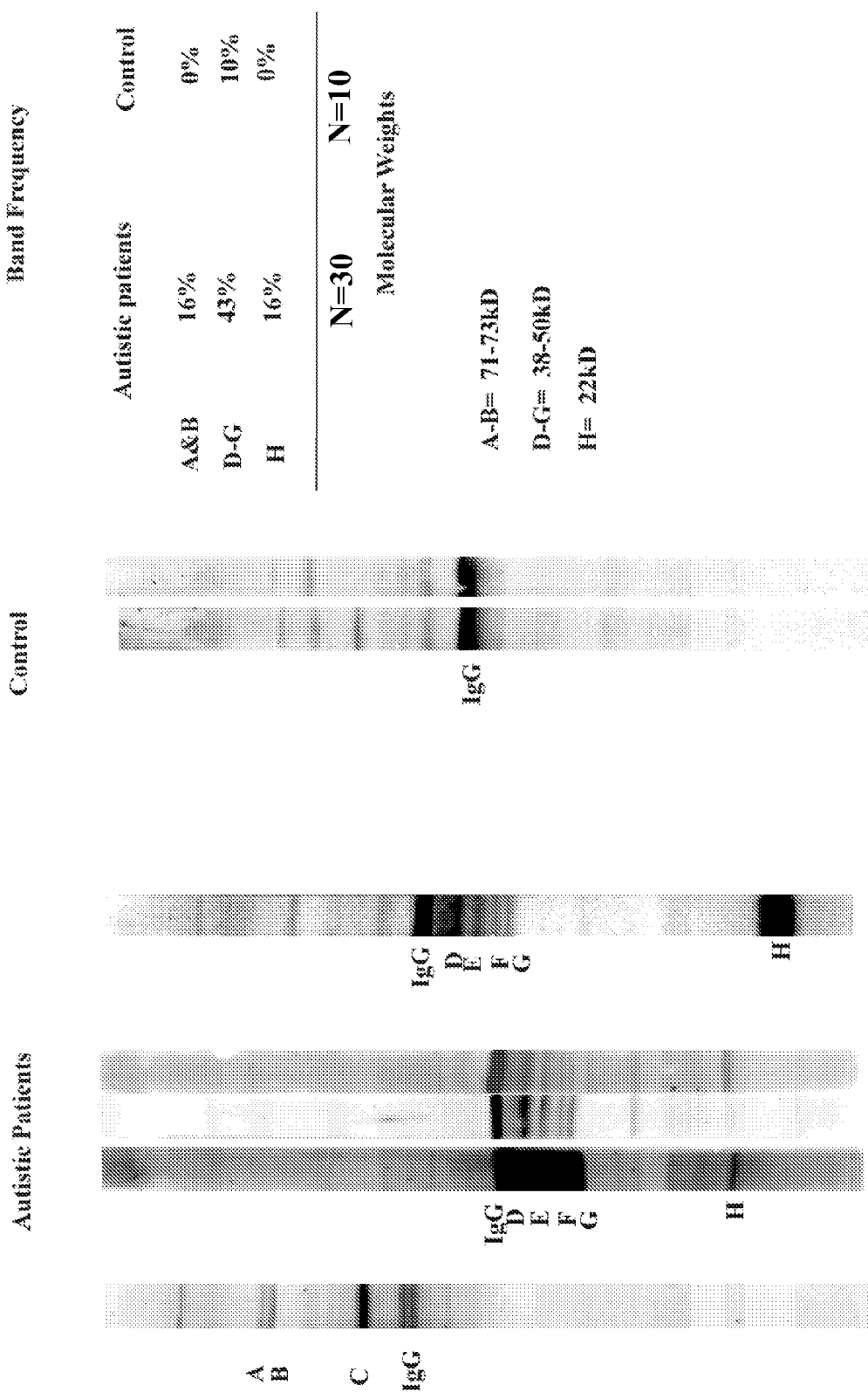
FIG. 2 illustrates a representative immunoblot of brain extract from the hypothalamus region exposed to serum from an individual having an ASD and from an individual not having an ASD. Serum dilutions are 1:1000.
Figure 3:
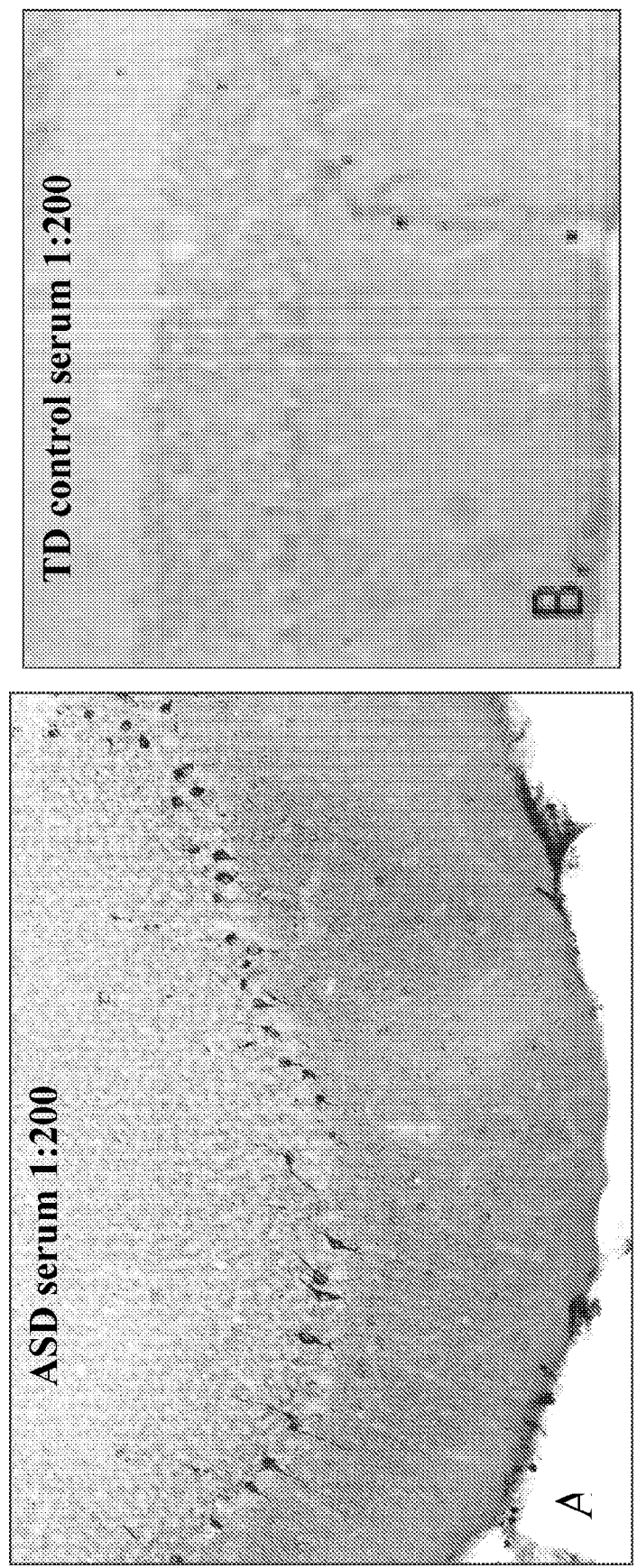
FIG. 3 illustrates a representative immunohistochemical pattern of in situ staining of a non-human primate cerebellum exposed to serum from an individual having an ASD and from an individual not having an ASD. Serum dilutions are 1:200. Exposing the cerebellar tissue to serum from an individual having an ASD results in a pattern of scattered, intensively stained cells just below the Purkinje layer of the cerebellum (granular layer). This pattern has been observed in 100% of replicates exposed to serum from individuals having ASD (n=7) and no replicates exposed to serum from individuals not having ASD (n=5).
Figure 4:
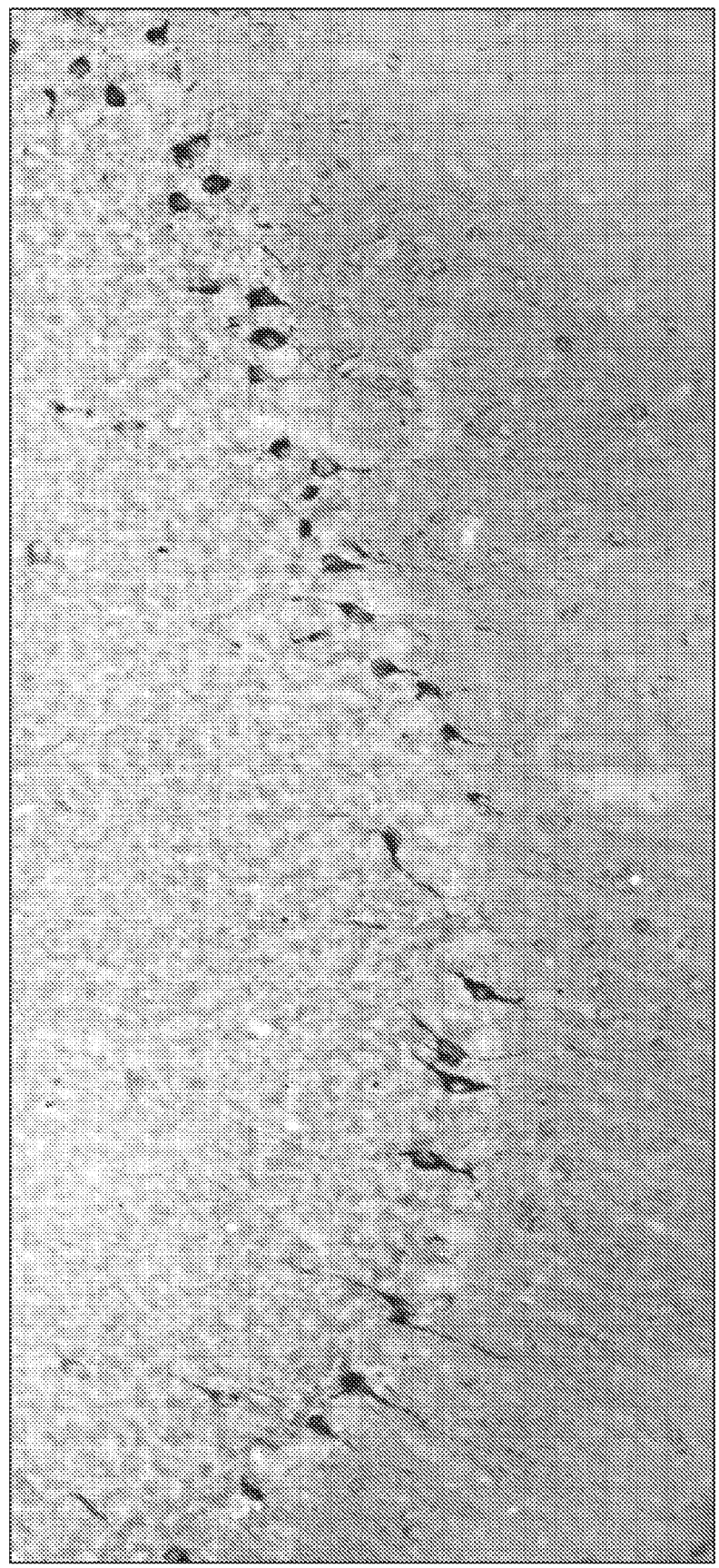
FIG. 4 illustrates the pattern of staining at the cellular level of cerebellar tissue exposed to serum from an individual having an ASD. Cell staining is intracytoplasmic and stains the length of the dendrites.
Figure 5:
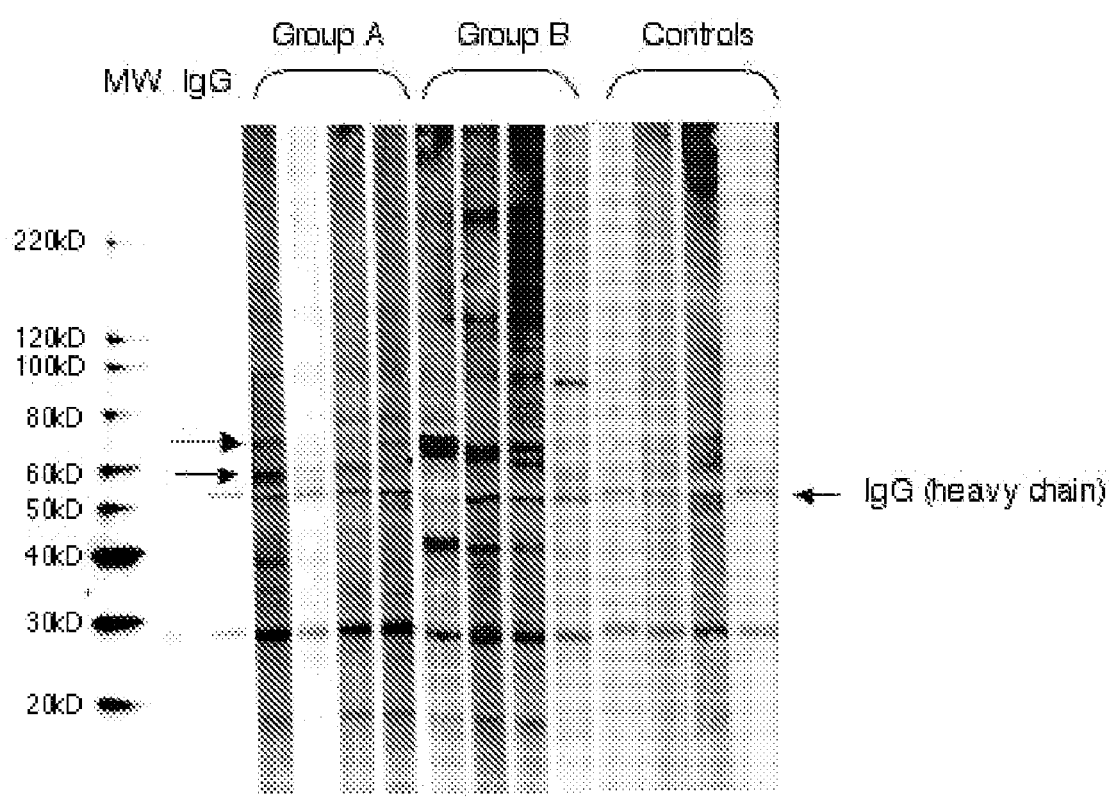
FIG. 5 illustrates a Western blot analysis of serum from mothers of children with autism against human fetal brain. Human fetal brain protein from 63 pooled samples from 20-40 weeks gestation was separated on a 4-15% gradient reducing gel and blotted onto nitrocellulose. Strips were cut from the blots and individually probed with serum diluted 1:400 obtained from 23 mothers who had more than one child with ASD. Samples were assigned to Groups A and B based upon the demonstrated banding pattern. Group A consisted primarily of samples whose pattern was represented by two bands at approximately 57 and 70 kD (designated by arrows). Group B largely consisted of serum specimens that produced a pattern with strong bands, often a doublet, between 60 and 70 kD, and a strong band at approximately 42 kD. There was sometimes overlap between the two groups with respect to the upper band (approximately 70 kD). This separation strategy allowed us to reduce the potential for dilution of the functional autoantibodies by grouping similarly reactive samples together. Note that the serum from the control mothers did not produce either pattern of reactivity.
Figure 6:
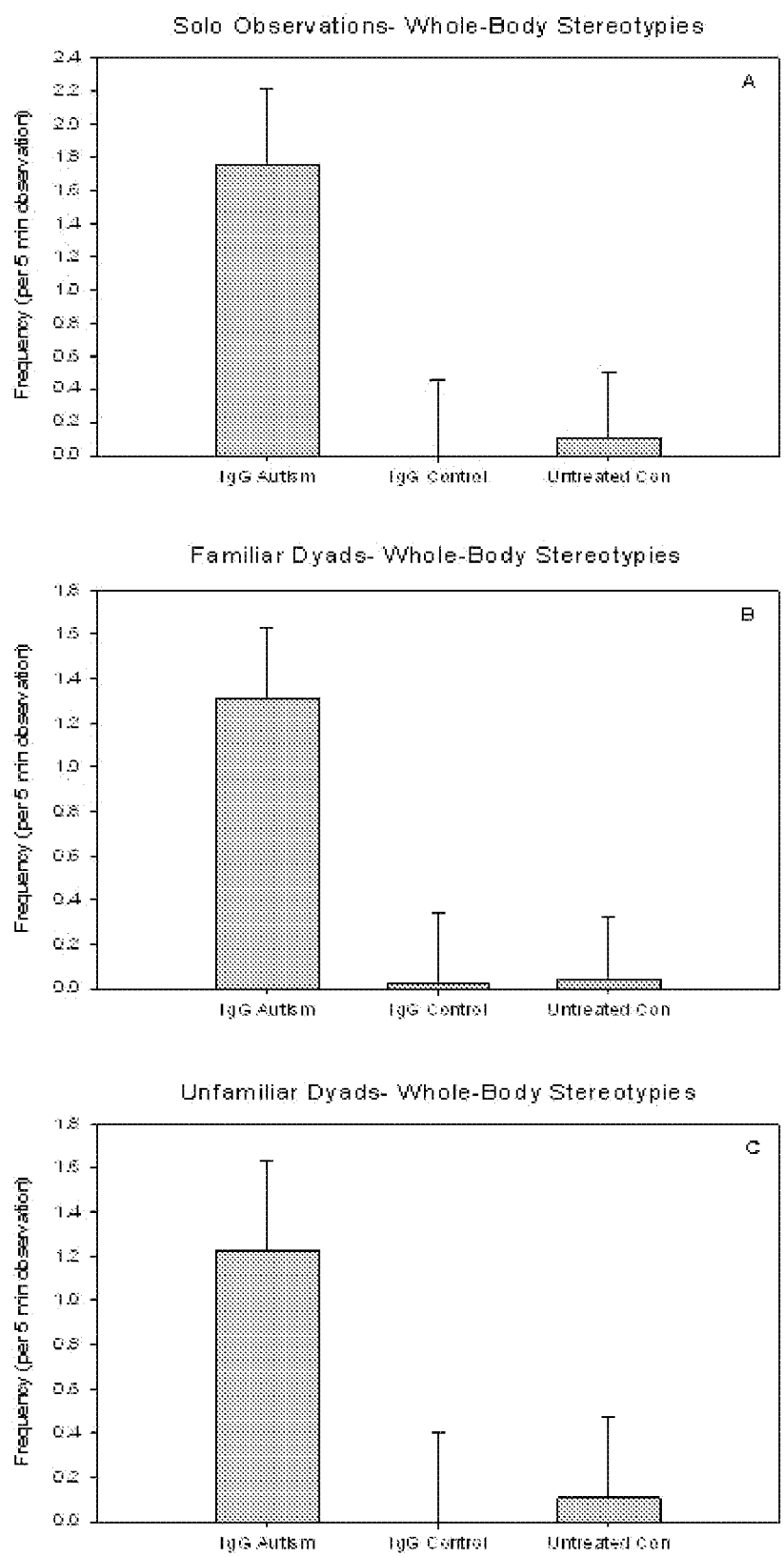
FIG. 6 illustrates mean episodes of whole-body stereotypies observed in maternal autism IgG treated, control IgG treated, and control untreated monkeys across three different observational paradigms. The maternal autism IgG treated monkeys displayed significantly more (p<0.05) episodes of whole-body stereotypies than both control IgG treated and control untreated monkeys during observations of the monkeys by themselves (A), with a familiar partner (B) and with an unfamiliar partner (C).

ANCOVAs, with age as the covariate were used for data analyses. Pairwise comparisons using the Sidak correction were then performed to determine group differences. The frequency of stereotypical episodes and the duration of stereotypies were not normally distributed and contained many zero values. Data were therefore transformed using ln (x+1) to normalize the data and respect theoretical assumptions before statistical analyses. Nontransformed data are presented in FIG. 2 to better illustrate the actual behavior of the animals.

Results

On the first 4 days immediately following weaning (at approximately 6 months of age), infants were tested in a task designed to assess preference for its mother over another adult female (Bauman, et al., *J Neurosci, supra*). Subjects were released in the center of a specially designed testing cage and allowed to freely move toward their mother, positioned on one end, or a familiar adult female from the subject's preweaning social group, placed on the other end. The adult females were separated from the testing enclosure by transparent plastic dividers. No differences were found in mother preference. However, a unique pattern of pacing across the length of the testing cage was observed in infants exposed to IgG from mothers of autistic children. Although when compared to the two control groups, the number of pacing events was not statistically significantly different (Frequency: $F_{2,9}=3.581$, p=0.072), the behavior stood out to our trained observers as being highly unusual for socially reared monkeys. This prompted a more intensive analysis of motor activity and stereotyped behaviors in other testing conditions.

One month following weaning (at approximately 7 months of age), each subject was removed from their social group and placed either alone or with a familiar partner in a large enclosure similar to their home environment. Each monkey was observed individually, and with each other monkey from its social group on two occasions. Behaviors were scored in real time during the testing session by trained observers from a predetermined list of both normal and abnormal monkey behaviors. Results demonstrated significantly higher frequencies of whole-body stereotypies in the maternal autism IgG treated monkeys compared to the control IgG treated and control untreated monkeys in both solo (Frequency: $F_{2,9}=6.608$, p=0.017) and paired (Frequency: $F_{2,9}=5.902$, p=0.023) conditions (FIG. 2A and B).

While the observed whole-body stereotypies included pacing, back-flipping, twirling, and swinging, 98% of the stereotypies were paces and back-flips. When the subject was engaged in a particular whole body stereotypy for more than 6 seconds, an extended stereotypy was scored. Significant differences were observed in the frequency and duration of extended stereotypies when animals were in the paired condition (Frequency: $F_{2,9}$=7.860, p=0.011; Duration: $F_{2,9}$=5.047, p=0.025).

Monkeys were also observed for behavioral differences during pairings with unfamiliar peers. One month following the pairings with familiar peers, monkeys were removed from their social groups and placed with one of four unfamiliar "stimulus" monkeys in the same large testing enclosures. Each test subject was paired with each "stimulus" monkey twice. Once again, results demonstrated a significantly higher frequency of whole-body stereotypies in the maternal autism IgG treated monkeys compared to control IgG treated and control untreated monkeys (Frequency: $F_{2,9}$=4.951, p=0.035; FIG. 2C).

Each monkey was also observed for behavioral differences within their social group on a biweekly basis during the weeks following the unfamiliar pairings. There were no behavioral differences between treatment groups in this familiar setting.

To summarize, the group of monkeys exposed prenatally to IgG from mothers of children with ASD demonstrated significantly more stereotypies than both monkeys prenatally exposed to the same amount of IgG from mothers of typically developing children and untreated control monkeys. Suggestions of this elevation in stereotypies first arose during the mother preference task that was conducted in the first 4 days following the permanent removal of the subject's mothers from the socialization groups. However, the increase in episodes of stereotyped behavior persisted and strengthened in the two months following weaning. Importantly, significantly increased stereotypies were observed consistently across three different testing paradigms: solo observations, familiar dyadic interactions and unfamiliar dyadic interactions.

Stereotypical behavior in monkeys is a sign of pathology. It can be brought on by, among other things, long-term individual housing conditions or environmental impoverishment (Lutz, et al., *Am J Primatol*, (2003) 60:1 and Mason, *Animal Behavior* (1991) 41:1015). Neither of these conditions applies to our experimental subjects. The monkeys in this study were maternally reared and socialized with other mother-infant pairs on a daily basis prior to weaning, and permanently socialized with 5 other monkeys following weaning. In addition, rather than housing the monkeys from each treatment group in separate enclosures, each social cohort included representation from each treatment group. Therefore, given that these stereotypies were only observed in the maternal autism IgG treatment group, they appear to be attributable to that particular form of IgG exposure. It is also important to note that no differences were observed between untreated control animals and animals treated with IgG from mothers of typically developing children.

Interestingly, the stereotypies were not as apparent prior to weaning and, while occasionally observed in their home cages, were not consistently present in their routine living condition. Rather, the stereotypies emerged when the monkeys were removed from their normal environment and placed in a novel social setting. It is important to emphasize that the IgG control group and the untreated control group had precisely the same rearing conditions as the autism IgG group. Moreover, in earlier studies involving neonatal brain lesions of the amygdala or hippocampal formation (Bauman, et al., *J Cogn Neurosci, supra* and Bauman, et al., *J Neurosci, supra*), no abnormal motor stereotypies were noted during this age range in any manipulated group.

Stereotypies have been considered one of the defining features of autism since the earliest descriptive accounts (Kanner, *Nervous Child* (1943) 2:217 and Asperger, *Archiv fur Psychiatrie und Nervenkrankheiten* (1944) 117:76). Along with the presence of stereotypies, individuals with autism are often described as having an "insistence on sameness" in their environment. A few studies have explored the effects of the environment on the rates of stereotyped behavior in autism. One study reported a progressive increase in stereotypies as unfamiliar toys followed by an unfamiliar passive adult were introduced into an empty room (Hutt, *Animal Behavior* (1965) 13:1). Another study demonstrated a significant increase in stereotypies with an unfamiliar versus a familiar therapist (Runco, et al., *J Sutism Dev Disord* (1986) 16:31). Although there remains limited information on stereotypical behavior in autism (Hendrickx, et al., *Teratology* (1988) 38:329), it is interesting to note that the treated monkeys in our study did not demonstrate increased stereotypical behavior in their long-term, stable social groups but only in novel environmental or social situations.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A method of diagnosing an autism spectrum disorder (ASD) in an individual, the method comprising:
   (a) contacting a first fluid tissue sample from the individual with brain extracts comprising at least one brain region selected from the group consisting of cerebellum, amygdala and orbital frontal cortex, wherein the first fluid tissue sample is blood, serum, plasma or cerebrospinal fluid, and wherein the brain extracts are from a non-living primate;
   (b) detecting binding of autoantibody from the fluid tissue sample to a neural antigen in the brain extracts, wherein binding of the autoantibody to a neural antigen in the extract of at least one of cerebellum, amygdala or orbital frontal cortex is indicative of an ASD;
   (c) contacting a second fluid tissue sample from the individual with a brain section comprising cerebellum from a non-living primate, wherein the second fluid tissue sample is blood, serum, plasma or cerebrospinal fluid; and
   (d) detecting a pattern of staining resulting from binding of the autoantibody to the brain section that is indicative of an ASD, wherein the pattern of staining is characterized by scattered intensively stained cells below the Purkinje layer of the cerebellum;
   whereby detecting the binding of the autoantibody and detecting the pattern of staining is indicative of the presence of an ASD, thereby diagnosing an ASD in the individual.

2. The method of claim 1, wherein brain cell types, stained within the brain section in step (d) are selected from the group consisting of granular layer cells, Golgi Type II cells and brain endothelial cells.

3. The method of claim 2, wherein the staining of brain cells in step (d) is intracytoplasmic and stains the length of the dendrites.

4. The method of claim 1, wherein the presence of the autoantibody determined in step (b) is determined by an immunoassay.

5. The method of claim 1, wherein the brain section in step (c) is from a whole brain.

6. The method of claim 1, wherein the brain extract in step (a) is from a non-human primate brain.

7. The method of claim 1, wherein the brain section in step (c) is from a non-human primate brain.

8. The method of claim 1, wherein the brain section in step (c) is a coronal, horizontal or sagittal section.

9. A method of determining an increased risk of an ASD in a mother's future offspring, the method comprising:
   (a) contacting a first fluid tissue sample taken from the mother during a prenatal period with brain extracts comprising at least one brain region selected from the group consisting of cerebellum, amygdala and orbital frontal cortex, wherein the first fluid tissue sample is blood, serum, plasma or cerebrospinal fluid, and wherein the brain extracts are from a non-living primate;
   (b) detecting binding of antibody from the fluid tissue sample to a neural antigen in the brain extracts, wherein binding of the antibody to a neural antigen in the extract of at least one of cerebellum, amygdala or orbital frontal cortex is indicative of an ASD;
   (c) contacting a second fluid tissue sample from the individual with a brain section comprising cerebellum from a non-living primate, wherein the second fluid tissue sample is blood, serum, plasma or cerebrospinal fluid; and
   (d) detecting a pattern of staining resulting from the binding of the antibody to the brain section that is indicative of an ASD, wherein the pattern of staining is characterized by scattered intensively stained cells below the Purkinje layer of the cerebellum;
   whereby detecting the presence of the antibody and the pattern of staining is indicative of an increased risk of an ASD in the mother's future offspring.

10. The method of claim 9, wherein brain cell types stained within the brain section in step (d) are selected from the group consisting of granular layer cells, Golgi Type II cells and brain endothelial cells.

11. The method of claim 10, wherein the staining of brain cells in step (d) is intracytoplasmic and stains the length of the dendrites.

12. The method of claim 9, wherein the presence of the antibody determined in step (b) is determined by an immunoassay.

13. The method of claim 9, wherein the brain section in step (c) is from a whole brain.

14. The method of claim 9, Wherein the brain extract in step (a) is from a non-human primate brain.

15. The method of claim 9, wherein the brain section in step (c) is from a non-human primate brain.

16. The method of claim 9, wherein the brain section in step (c) is from a fetal brain.

17. The method of claim 9, wherein the brain section in step (c) is a coronal, horizontal or sagiffal section.

18. The method of claim 9, wherein the neural antigen is a fetal neural antigen.

* * * * *